United States Patent

Bosmans et al.

Patent Number: 6,159,982
Date of Patent: Dec. 12, 2000

[54] 2,4-DIAMINOPYRIMIDINE DERIVATES AS DOPAMINE D4 RECEPTOR ANTAGONIST

[75] Inventors: Jean-Paul René Marie André Bosmans, Rijkevorsel; Christopher John Love, Deurne; Guy Rosalia Eugène Van Lommen, Berlaar, all of Belgium

[73] Assignee: Janssen Pharmaceutica N. V., Belgium

[21] Appl. No.: 09/180,364

[22] PCT Filed: May 2, 1997

[86] PCT No.: PCT/EP97/02506

§ 371 Date: Nov. 9, 1998

§ 102(e) Date: Nov. 9, 1998

[87] PCT Pub. No.: WO97/43279

PCT Pub. Date: Nov. 20, 1997

[30] Foreign Application Priority Data

May 10, 1996 [EP] European Pat. Off. .............. 96201283

[51] Int. Cl.[7] ...................... C07D 401/12; C07D 405/14; C07D 401/14; A61K 31/505
[52] U.S. Cl. ............................................. 514/275; 544/324
[58] Field of Search .............................. 544/324; 514/275

[56] References Cited

FOREIGN PATENT DOCUMENTS

| 0 379 806 | 8/1990 | European Pat. Off. . |
| 0 532 178 | 3/1993 | European Pat. Off. . |
| WO 93/17017 | 9/1993 | WIPO . |
| WO 96/10018 | 4/1996 | WIPO . |

OTHER PUBLICATIONS

Ross, Chapeter 2 in Goodman and Gilman's The Pharmacological Basis of Therapeutics, 8th Ed., Pergamon Press, P. 33–35, 1990.

Schotte et al. Psychopharmacology 124:57–73, 1996.

*Primary Examiner*—Mukund J. Shah
*Assistant Examiner*—Hong Liu
*Attorney, Agent, or Firm*—Mary Appollina

[57] ABSTRACT

The present invention concerns the compounds of formula

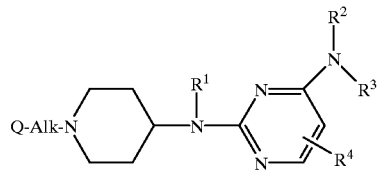

(I)

the N-oxide forms, the pharmaceutically acceptable acid addition salts and stereochemically isomeric forms thereof, wherein Alk is $C_{1-6}$alkanediyl or $C_{3-6}$alkenediyl; $R^1$ is hydrogen or $C_{1-4}$alkyl; $R^2$ and $R^3$ each independently are hydrogen, $C_{1-6}$alkyl or $C_{3-7}$cycloalkyl; or $R^2$ and $R^3$ may also be taken together with the nitrogen atom to which they are attached, thus forming a pyrrolidine, a piperidine or a perhydro azepine ring; $R^4$ is hydrogen or halo; Q is aryl, aryloxy, di(aryl)methyl or heteroaryl; aryl is naphthyl or phenyl, said naphthyl and phenyl may optionally be substituted; and heteroaryl is quinolinyl, isoquinolinyl, pyridinyl, thienyl, indolyl, 2,3-dihydro-1,4-benzodioxinyl, 2,3-dihydro-benzofuranyl or benzodioxolanyl; said heteroaryls may optionally be substituted: it further relates to processes for their preparation, compositions comprising them as well as their use as a medicine; compounds of formula (I) containing a radioactive isotope; a process of marking dopamine $D_4$ receptor sites; and a process for imaging an organ are disclosed.

3 Claims, No Drawings

2,4-DIAMINOPYRIMIDINE DERIVATES AS DOPAMINE D4 RECEPTOR ANTAGONIST

CROSS REFERENCE TO RELATED APPLICATIONS

This application is a National Stage application under 35 U.S.C. § 371 of PCT/EP97/02506 filed May 2, 1997, which claims priority from EP 96.201.283.7, filed May 10, 1996.

The present invention concerns 2,4-diaminopyrimidine derivatives; it further relates to processes for their preparation, compositions comprising them, as well as their use as a medicine. The compounds of the present invention exhibit specific dopamine $D_4$ receptor antagonism and may particularly be useful as antipsychotics, especially in the treatment and/or prevention of psychotic disorders such as schizophrenia. In addition, the present invention concerns compounds of formula (I) containing a radioactive isotope; a process of marking dopamine $D_4$ receptor sites; and a process for imaging an organ.

It is generally accepted knowledge that dopamine receptors are important for many biochemical functions in the animal body. For example, altered functions of these receptors not only participate in the genesis of psychosis, but also of anxiety, emesis, motoric functions, addiction, sleep, feeding, learning, memory, sexual behaviour, regulation of immunological responses and blood pressure. Since dopamine receptors control a great number of pharmacological events, some of which are thus far unknown, there is a possibility that compounds which exhibit a specific binding affinity for the $D_4$ receptor may exert a wide range of therapeutic effects in humans.

EP-A-0,379,806, published on Aug. 1, 1990, discloses N-[2-[(4-piperidinyl)amino]-4-pyrimidinyl]benzamides and generically describes 2-[(4-piperidinyl)amino]-4-(mono- or di(alkyl)amino)-pyrimidine derivatives, all having therapeutic potential in neurological diseases of the peripheral and central nervous systems of animals. Further, WO 93/17017 published on Sep. 2, 1993, generically discloses N-[1-(2,3-dihydro-(1,4-benzodioxin or benzofuranyl)-2-ylalkyl)-4-piperidinyl]-2,4-diaminopyrimidine derivatives showing 5-HT$_{1\text{-like}}$ antagonistic activity.

The 2,4-diaminopyrimidine derivatives of the present invention surprisingly show a high degree of dopamine $D_4$ receptor binding affinity. Moreover, the present compounds have a selective affinity for the dopamine $D_4$ receptor over other dopamine receptors in the human body. The subject compounds also show variable affinity for other receptors such as, for example, the σ-binding site.

The present invention concerns compounds having the formula

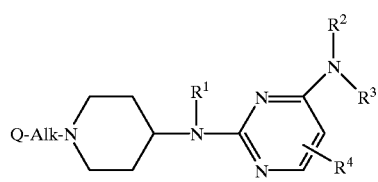

(I)

the N-oxide forms, the pharmaceutically acceptable acid addition salts and stereochemically isomeric forms thereof, wherein Alk is $C_{1-6}$alkanediyl or $C_{3-6}$alkenediyl;
$R^1$ is hydrogen or $C_{1-4}$alkyl;
$R^2$ and $R^3$ each independently are hydrogen, $C_{1-6}$alkyl or $C_{3-7}$cycloalkyl; or
$R^2$ and $R^3$ may also be taken together with the nitrogen atom to which they are attached, thus forming a pyrrolidine, a piperidine or a perhydro azepine ring;
$R^4$ is hydrogen or halo;
Q is aryl, aryloxy, di(aryl)methyl or heteroaryl;
aryl is naphthyl or phenyl, said naphthyl and phenyl may optionally be substituted with one, two or three substituents selected from halo, hydroxy, $C_{1-4}$alkyl, $C_{1-4}$alkyloxy, $C_{1-4}$alkylcarbonyl, haloC$_{1-4}$alkyl, nitro, amino, cyano and phenyl; and
heteroaryl is quinolinyl, isoquinolinyl, pyridinyl, thienyl, indolyl, 2,3-dihydro-1,4-benzodioxinyl, 2,3-dihydrobenzofuranyl or benzodioxolanyl; said heteroaryls may optionally be substituted with one, two or three substituents selected from halo, hydroxy, $C_{1-4}$alkyl, $C_{1-4}$alkyloxy, $C_{1-4}$alkylcarbonyl, haloC$_{1-4}$alkyl and phenyl.

As used in the foregoing definitions and hereinafter, halo is generic to fluoro, chloro, bromo and iodo: $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; $C_{1-6}$alkanediyl defines bivalent straight and branched chain saturated hydrocarbon radicals having from 1 to 6 carbon atoms such as, for example, 1,1-methanediyl, 1,2-ethanediyl, 1,3-propanediyl, 1,4 butanediyl, 1,5-pentanediyl, 1,6-hexanediyl, 1,2-propanediyl, 2,3-butanediyl and the like; $C_{3-6}$alkenediyl defines bivalent straight and branched chain hydrocarbon radicals containing one double bond and having from 3 to 6 carbon atoms such as, for example, 2-propen-1,3-diyl, 3-buten-1,4-diyl, 2-buten-1,4-diyl, 2-penten-1,5-diyl, 3-penten-1,5-diyl, 3-methyl-2-buten-1,4-diyl, 3-hexen-1,6-diyl and the like: and the carbon of said $C_{3-6}$alkenediyl connected to the nitrogen atom of the piperidine ring preferably is saturated; haloC$_{1-4}$alkyl is defined as polyhalo-substituted $C_{1-4}$alkyl, in particular $C_{1-4}$alkyl substituted with 1 to 6 halogen atoms, more in particular difluoro- or trifluoromethyl.

The heteroaryl group represented by Q may be attached to the remainder of the molecule of formula (I) through any ring carbon or heteroatom as appropriate. Thus, for example, when the heteroaryl group is benzodioxolanyl, it may be a 2-benzodioxolanyl, 4-benzodioxolanyl, 5-benzodioxolanyl, 6-benzodioxolanyl and 7-benzodioxolanyl; when it is quinolinyl, it may be 2-quinolinyl, 3-quinolinyl, 4-quinolinyl, 5-quinolinyl, 6-quinolinyl, 7-quinolinyl and 8-quinolinyl; when it is 2,3-dihydro-benzofuranyl, it may be 2,3-dihydro-benzofuran-2-yl, 2,3-dihydro-benzofuran-3-yl, 2,3-dihydro-benzofuran-4-yl, 2,3-dihydro-benzofuran-5-yl, 2,3-dihydro-benzofuran-6-yl and 2,3-dihydro-benzofuran-7-yl.

The pharmaceutically acceptable acid addition salts as mentioned hereinabove are meant to comprise the therapeutically active non-toxic acid addition salt forms which the compounds of formula (I) are able to form. Said salts can be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

Preferably, $R^1$ is $C_{1-4}$alkyl.

Preferably, $R^2$ is $C_{1-6}$alkyl or $C_{3-7}$cycloalkyl and $R^3$ is hydrogen or $C_{1-6}$alkyl, or $R^2$ and $R^3$ are taken together with the nitrogen atom to which they are attached, thus forming a pyrrolidine ring.

Preferably, Alk is a straight chained $C_{1-6}$alkanediyl or a straight chained $C_{3-6}$alkenediyl, more in particular, Alk is methylene, 1,3-propanediyl or 1,4-butanediyl. Suitably, aryl is 2-naphthyl, 3-naphthyl, phenyl or mono- or disubstituted phenyl. Suitably, heteroaryl is optionally substituted 2-quinolinyl, 3-pyridyl, 4-pyridyl, 2-thienyl, 3-indolyl, 2,3-dihydro-1,4-benzodioxin-2-yl, 2,3-dihydrobenzofuran-5-yl or 5-benzodioxolanyl.

A first group of particular compounds are those compounds of formula (I) wherein Alk is a straight chained $C_{1-6}$alkanediyl and Q is optionally substituted phenyl, 2-naphthyl, 2-quinolinyl, 2,3-dihydrobenzofuran-5-yl or 5-benzodioxolanyl.

A second group of particular compounds are those compounds of formula (I) wherein $R^1$ is $C_{1-4}$alkyl; $R^2$ is $C_{1-6}$alkyl or $C_{3-7}$cycloalkyl and $R^3$ is hydrogen, $C_{1-6}$alkyl; or $R^2$ and $R^3$ form a pyrrolidine ring when taken together with the nitrogen atom to which they are attached.

Interesting compounds are those compounds of formula (I) wherein $R^4$ is hydrogen.

Preferred compounds are those particular compounds wherein $R^1$ is methyl; $R^2$ is methyl, ethyl, propyl or cyclopropyl and $R^3$ is hydrogen, methyl or ethyl; or $R^2$ and $R^3$ form a pyrrolidine ring when taken together with the nitrogen atom to which they are attached; Alk is methylene, and Q is optionally substituted phenyl, 2-naphthyl, 2-quinolinyl, 2,3-dihydrobenzofuran-5-yl or 5-benzodioxolanyl.

More preferred compounds are those preferred compounds wherein $R^2$ is methyl, ethyl or cyclopropyl and $R^3$ is hydrogen or methyl; or $R^2$ and $R^3$ form a pyrrolidine ring when taken together with the nitrogen atom to which they are attached.

Most preferred compounds are $N^4$-cyclopropyl-$N^2$-methyl-$N^2$-[1-(phenylmethyl)-4-piperidinyl]-2,4-pyrimidinediamine;

$N^2$-[1-(1,3-benzodioxol-5-ylmethyl)-4-piperidinyl]-$N^4$-ethyl-$N^2$-methyl-2,4-pyrimidinediamine;

$N^2$-[1-(1,3-benzodioxol-5-ylmethyl)-4-piperdinyl]-$N^4$-cyclopropyl-$N^2$-methyl-2,4-pyrimidinediamine;

$N^2$-[1-[(4-chlorophenyl)methyl]-4-piperidinyl]-$N^2$,$N^4$,$N^4$-trimethyl-2,4-pyrimidine diamine;

$N^2$-[1-[(3-fluorophenyl)methyl]-4-piperidinyl]-$N^2$,$N^4$,$N^4$-trimethyl-2,4-pyrimidinediamine;

$N^2$,$N^4$,$N^4$-trimethyl-$N^2$-[1-[[4-(trifluoromethyl)phenyl]methyl]-4-piperidinyl]-2,4-pyrimidinediamine;

$N^2$,$N^4$,$N^4$-trimethyl-$N^2$-[1-[(4-methylphenyl)methyl]-4-piperidinyl]-2,4-pyrimidinediamine;

$N^2$,$N^4$,$N^4$-trimethyl-$N^2$-[1-[(3-methylphenyl)methyl]-4-piperidinyl]-2,4-pyrimidinediamine; the stereochemically isomeric forms and the pharmaceutically acceptable addition salts thereof.

Compounds of formula (I) can generally be prepared by N-alkylating an intermediate of formula (III) with an intermediate of formula (II), wherein W represents an appropriate reactive leaving group such as, for example, a halogen. The reaction can be performed in a reaction-inert solvent such as, for example, methyl isobutylketone, N,N-dimethylacetamide or N,N-dimethylformamide, in the presence of a suitable base such as, for example, sodium carbonate or triethylamine, and optionally in the presence of potassium iodide. Stirring may enhance the rate of the reaction. The reaction may conveniently be carried out at a temperature ranging between room temperature and reflux temperature.

Compounds of formula (I) wherein Alk is attached to the nitrogen of the piperidine ring by a carbon atom bearing at least one hydrogen atom, said compounds being represented by formula (I-a) and said Alk being represented by Alk'H, can be prepared by reductively N-alkylating an intermediate of formula (III) with an aldehyde or ketone of formula Q—Alk'=O (IV), said Q—Alk'=O being derived from Q—Alk'$H_2$ by replacing two germinal hydrogen atoms by an oxo group.

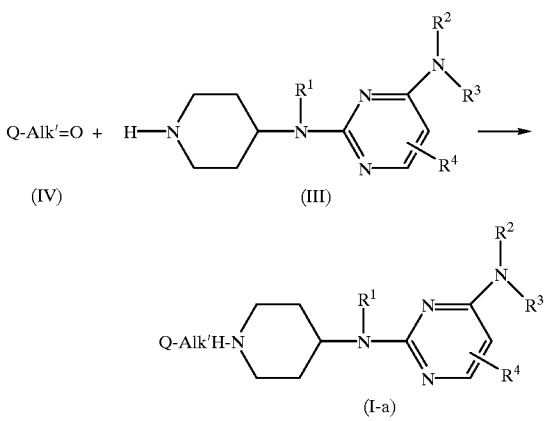

Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Further, compounds of formula (I) can be prepared by reacting an intermediate of formula (V) with an intermediate of formula (VI), wherein $W^1$ is a suitable leaving group such as, e.g. halo, following art-known N-alkylation procedures.

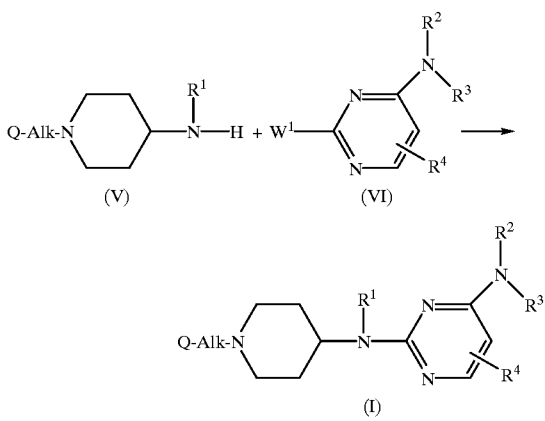

The compounds of formula (I) may be also converted into other compounds of formula (I) following art-known transformation reactions. For instance, compounds of formula (I) wherein $R^4$ is hydrogen, said compounds being represented by formula (I-b-1), may be converted into compounds of formula (I) wherein $R^4$ is a halogen atom, said compounds being represented by formula (I-b-2). For instance, an iodine atom may be introduced in the 5-position of the pyrimidine ring of a compound of formula (I-b-1) by reacting said compound with a mixture of benzyltrimethylammoniumchloride and iodinechloride, or a functional analogue thereof. Alternatively, the introduction of an iodine atom in the 5-position of the pyrimidine ring of a compound of formula (I-b-1) may be established by reacting said compound with a mixture of a peroxide and $I_2$. The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For instance, intermediates of formula (III) may be prepared according to the procedures described in WO-93/17017.

In the following paragraphs there are described several methods of preparing the intermediates employed in the foregoing preparations.

Intermediates of formula (III) can be prepared by reacting an intermediate of formula (VII), wherein $P^1$ is a protective group such as, e.g. alkyloxycarbonyl with an intermediate of formula (VI), following art-known N-alkylation methods, and subsequently removing $P^1$.

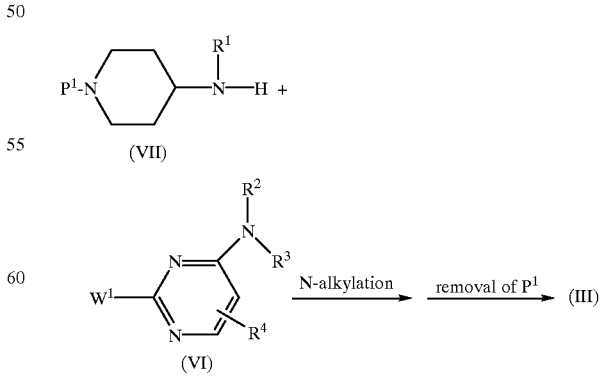

Intermediates of formula (V) can be prepared by reacting an intermediate of formula (VIII), wherein $P^2$ is a suitable protecting group such as, e.g. alkyloxycarbonyl, with an intermediate of formula (II), following art-known N-alkylation methods, and subsequently removing $P^2$.

Q-Alk-W +

(II)

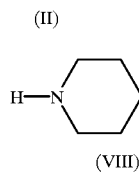

(VIII)

$\xrightarrow{\text{N-alkylation}}$ $\xrightarrow{\text{removal of } P^2}$ (V)

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

An alternative manner of separating the enantiomeric forms of the compounds of formula (I) and intermediates involves liquid chromatography, in particular liquid chromatography using a chiral stationary phase.

Pure stereochemically isomeric forms of the compounds of formula (I) may also be obtained from the pure stereochemically isomeric forms of the appropriate intermediates and starting materials, provided that the intervening reactions occur stereo-specifically. The pure and mixed stereochemically isomeric forms of the compounds of formula (I) are intended to be embraced within the scope of the present invention.

The compounds of formula (I), the N-oxides, the pharmaceutically acceptable acid addition salts and stereochemically isomeric forms thereof, are potent antagonists of the dopamine $D_4$ receptor, i.e. they show a high degree of dopamine $D_4$ receptor binding affinity thus inhibiting the binding of an endogeneous ligand, in particular dopamine, to the dopamine $D_4$ receptor, as is demonstrated in the pharmacological example described hereinafter. The antagonistic effect of the binding of the present compounds to the dopamine $D_4$ receptor was confirmed in signal-transduction assays.

The present compounds show interesting activity in the so-called "differential reinforcement test low rate 72 seconds"-test (DRL-72) which is an in vivo test where most clinically active antidepressants given at high doses show activity. In said test, rats can obtain food by pressing a lever only when they have waited a full 72 seconds between two lever presses. The present $D_4$ antagonists induce a more efficient behaviour of the rats whereas untreated animals find it difficult to control their impulsive tendency to press the lever and to subordinate it to appropriate timing so as to maximize their award. The usefulness of this DRL-72 test as a model for specific $D_4$ antagonists such as the present compounds is further supported by the fact that (a) Manki et al. (Journal of Affective Disorders 40 (1996), 7–13) found that there is a significant association between the $D_4$ receptor gene polymorphism and mood disorders, and (b) by the fact that $D_4$ receptors are known to be most dense in hippocampus, entorhinal and cerebral cortex in the primates, humans as well as rodents.

Antagonizing the dopamine $D_4$ receptor will suppress or relieve a variety of symptoms associated with phenomena induced by the activation, in particular the excessive activation, of said receptor. Consequently, the ability of the present compounds to alter dopamine $D_4$ mediated neurotransmission makes them of potential use in the treatment and/or prevention of a variety of disorders associated therewith such as sleep disorders, sexual disorders, thought disorders, impaired information processing, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, gastrointestinal disorders, obesity, emesis. bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De la Tourette's syndrome and other hyperkinesias, dementia, ischemia, movement disorders such as akathesia, hypertension and diseases caused by a hyperactive immune system such as allergies and inflammation.

The compounds of the present invention distinctively show affinity for the dopamine $D_4$ receptor in comparison with other dopamine receptors such as, for example, the dopamine $D_2$ receptor. Such a dissociation between dopamine $D_4$ receptor antagonizing activity and other dopamine receptor activity may be of additional use in the treatment and/or prevention of the above-mentioned disorders. For example, Van Tol et al. (Nature 1991, 350, 610–614) suggested that compounds which can interact selectively with the dopamine $D_4$ receptor, whilst having a less pronounced action at the dopamine $D_2$ receptor, might have the same beneficial level of antipsychotic activity as classical antipsychotics with the additional benefit of being less prone to the undesired extrapyramidal or neuroendocrine side-effects of classical antipsychotics. It is therefore that the present compounds are particularly useful as antipsychotics, especially in the treatment and/or prevention of psychotic disorders such as schizophrenia.

In addition to their potency to antagonize the dopamine $D_4$ receptor, the subject compounds also show variable affinity for other receptors such as, for example, the σ-binding site.

In view of the usefulness of the subject compounds in the treatment and/or prevention of disorders associated with the excessive activation of the dopamine $D_4$ receptor, in particular in the treatment of psychotic disorders such as schizophrenia, the present invention provides a method of treating warm-blooded animals suffering from such diseases, said method comprising the systemic administration of a dopamine $D_4$ receptor antagonizing amount of a compound of formula (I), a N-oxide or a pharmaceutically acceptable acid addition salt thereof.

The present invention thus also relates to compounds of formula (I) as defined hereinabove for use as a medicine. Further, the present invention also relates to the use of a compound of formula (I) for the manufacture of a medicament for treating psychotic disorders.

The term "dopamine $D_4$ receptor antagonizing amount", as used herein, refers to an amount sufficient to inhibit the binding of an endogeneous ligand, in particular dopamine, to the dopamine $D_4$ receptor. Those of skill in the treatment of the disorders as mentioned hereinabove could determine that an effective dopamine $D_4$ receptor antagonizing daily amount would be from about 0.01 mg/kg to about 10 mg/kg body weight, more preferably from about 0.04 mg/kg to about 4 mg/kg body weight. The compounds may be administered on a regimen of 1 to 4 times per day.

In order to alleviate the symptoms of psychotic disorders such as schizophrenia without causing undesired side-effects, the dosage level of the compound according to the invention is ideally selected such that the dose administered is effective in substantially completely blocking the dopamine $D_4$ receptor while displaying a favourable dopamine $D_2$ receptor occupancy causing no or negligible undesired extrapyramidal or neuroendocrine side-effects.

If desired, the compounds according to this invention may be co-administered with another antipsychotic, for example one producing its effects via one or more of the following mechanisms: dopamine $D_2$ receptor blockade, 5-$HT_2$ receptor blockade, 5-$HT_{1A}$ agonism and 5-$HT_3$ antagonism. In such circumstances, an enhanced anti-psychotic effect may be envisaged without a corresponding increase in side-effects such as those caused by, for example, strong dopamine $D_2$ receptor blockade; or a comparable antipsychotic effect with reduced side-effects may alternatively be envisaged. Such co-administration may be desirable where a patient is already established on a, for example, anti-schizophrenic treatment regime involving conventional anti-schizophrenic medicaments.

For administration purposes, the subject compounds may be formulated into various pharmaceutical forms. To prepare the pharmaceutical compositions of this invention, an effective dopamine $D_4$ receptor antagonizing amount of the particular compound, as acid addition salt or in its free base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed. such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil. soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of the compounds of formula (I) due to their increased water solubility over the corresponding free base form, are more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Due to their high degree of specificity to the dopamine $D_4$ receptor, the compounds of formula (I) as defined above, are also useful to mark or identify receptors, in particular dopamine $D_4$ receptors. To this purpose. the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine, or those compounds having at least one $^{11}$C-atom or tritium atom.

One particular group consists of those compounds of formula (I) wherein Q is aryl or heteroaryl substituted with a radioactive halogen atom, or those compounds wherein $R^4$ is a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I), in particular, the reactions for converting compounds of formula (I-b-1) to compounds of formula (I-b-2).

Preferred labelled compounds are those compounds of formula (I), wherein Q is aryl or heteroaryl substituted with $^{123}$I, $^{125}$I, $^{75}$Br, $^{76}$Br, $^{77}$Br or $^{18}$F; or wherein $R^4$ is $^{123}$I, $^{125}$I, $^{75}$Br, $^{76}$Br, $^{77}$Br or $^{18}$F. More preferred are those compounds of formula (I) wherein $R^4$ is $^{125}$I.

Another interesting form of radiolabelling a compound of formula (I) is by substituting a carbon atom by a $^{11}$C-atom or the substitution of a hydrogen atom by a tritium atom. Introducing such a $^{11}$C-atom is conveniently carried out by N-alkylating a compound of formula (I), wherein $R^1$, $R^2$ and/or $R^3$ are hydrogen using a $^{11}$C-labelled alkylating reagent. Tritium radiolabelled compounds of formula (I-a) can be prepared by reductively N-alkylation intermediates of formula (III) with intermediates of formula (IV) in the presence of $^3H_2$-gas as reducing agent and in combination with a suitable catalyst. Those compounds of formula (I) containing a halogen atom may also be suitably converted to tritium radiolabelled compounds of formula (I) by exchanging the halogen atom with $^3H_2$-gas in the presence of a suitable catalyst such as, for example palladium on activated carbon.

Hence, said radiolabelled compounds of formula (I) can be used in a process of specifically marking dopamine $D_4$ receptor sites in biological material. Said process comprises the steps of (a) radiolabelling a compound of formula (I), (b) administering this radiolabelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs. The radiolabelled compounds of formula (I) are also useful as agents for screening whether a test compound has the ability to occupy or bind to a dopamine $D_4$ receptor site. The degree to which a test compound will displace a compound of formula (I) from the dopamine $D_4$ receptor site will show the test compound ability as either an agonist, an antagonist or a mixed agonist/antagonist of a dopamine $D_4$ receptor. When used in in vivo assays, the radiolabelled compounds are administered in an appropriate composition to an animal and the location of said radiolabelled compounds is detected using imaging techniques, such as, for instance. Single Photon Emission Computerized Tomography (SPECT) or Positron Emission Tomography (PET) and the like. In this manner the distribution of dopamine $D_4$ receptor sites throughout the body can be detected and organs containing dopamine $D_4$ receptor sites such as, for example, the brain, can be visualized by the imaging techniques mentioned hereinabove. This process of imaging an organ by administering a radiolabelled compound of formula (I), which binds to the dopamine $D_4$ receptor sites and detecting the emissions from the radioactive compound also constitutes a part of the present invention.

The following examples are intended to illustrate and not to limit the scope of the present invention.

A. Preparation of the intermediates

EXAMPLE A.1 a) A mixture of ethyl 4-(methylamino)-1-piperidinecarboxylate (111.75 g) and 2-chloro-N,N-dimethyl-4-pyrimidinamine (47.3 g) is stirred and heated in an oil-bath for 22 hours at 120° C. The reaction mixture is cooled and the product is taken up in trichloromethane (500 ml). Water (300 ml) is added and the layers are separated. The organic phase is washed with water (200 ml), dried, filtered and evaporated. The residue solidifies on triturating in petroleumether. The product is filtered off and crystallized from diisopropyl ether (390 ml). After cooling to 0° C., the product is filtered off and dried, yielding 55.5 g (59.7%) of ethyl 4-[[4-dimethylamino-2-pyrimidinyl]methylamino]-1-piperidinecarboxylate (intermediate 1).

b) A mixture of intermediate 1 (52.5 g), potassium hydroxide (95.4 g) and 2-propanol (950 ml) is stirred and refluxed for 18 hours. The reaction mixture is evaporated and water (900 ml) are added to the residue. The whole is stirred for 30 minutes in a boiling water-bath and evaporation is continued till all traces of 2-propanol are removed. After cooling, the product is extracted twice with dichloromethane (270 ml). The combined extracts are washed with 280 parts of diisopropyl ether (390 ml). After cooling to 0° C., the product is filtered off and dried, yielding 29 g (72.5%) of $N^2,N^4,N^4$-trimethyl-$N^2$-(4-piperidinyl)-2,4-pyrimidinediamine (intermediate 2).

In a similar way were prepared:

$N^4$-ethyl-$N^2$-methyl-$N^2$-(4-piperidinyl)-2,4-pyrimidinediamine (interm. 3);

$N^4$-cyclopropyl-$N^2$-methyl-$N^2$-(4-piperidinyl)-2,4-pyrimidinediamine (interm. 4);

N-methyl-N-(4-piperidinyl)-4-(1-pyrrolidinyl)-2-pyrimidinamine (interm. 5);

$N^2,N^4$-dimethyl-$N^2$-(4-piperidinyl)-2,4-pyrimidinediamine (interm. 6);

$N^2$-butyl-$N^4,N^4$-dimethyl-$N^2$-(4-piperidinyl)-2,4-pyrimidinediamine (interm. 7);

$N^4,N^4$-dimethyl-$N^2$-methyl-$N^2$-(4-piperidinyl)-2,4-pyrimidinediamine (interm. 8);

$N^2$-methyl-$N^2$-(4-piperidinyl)-$N^4,N^4$-dipropyl-2,4-pyrimidinediamine (interm. 9);

$N^2$-ethyl-$N^4,N^4$-dimethyl-$N^2$-(4-piperidinyl)-2,4-pyrimidinediamine (interm. 10);

$N^4,N^4$-dimethyl-$N^2$-(4-piperidinyl)-2,4-pyrimidinediamine (interm. 11);

$N^2$-methyl-$N^2$-(4-piperidinyl)-2,4-pyrimidinediamine (interm. 12);

$N^4$-butyl-$N^2$-methyl-$N^2$-(4-piperidinyl)-2,4-pyrimidinediamine (interm. 13); and $N^2$-methyl-$N^4$-(1-methylethyl)-$N^2$-(4-piperidinyl)-2,4-pyrimidinediamine (interm. 14).

EXAMPLE A.2

A solution of intermediate (7) (6.8 g) in 2-propanol (32 ml) was acidified with concentrated nitric acid. The crystallized product was filtered off and dried, yielding 7 g (70.7%) of $N^2$-butyl-$N^4,N^4$-dimethyl-$N^2$-(4-piperidinyl)-2,4-pyrimidinediamine dinitrate (interm. 15; mp. 168.6° C.).

In a similar way, the dinitrate salt of intermediates (8) and (9) were prepared.

B. Preparation of the final compounds

EXAMPLE B.1

A mixture of bromomethylbenzene (0.06 g), intermediate 3 (0.100 g) and sodium carbonate (0.100 g) in 4-methyl-2-pentanone (2 ml) was stirred overnight at 60° C. The mixture was filtered, diluted with $CH_2Cl_2$ until a 15 ml total volume was obtained, then purified by high-performance liquid chromatography over silica gel (eluent: A=$CH_2Cl_2$ and B=$CH_2Cl_2/CH_3OH$ 90/10: from 100% A to 100% B over 20 minutes; 125 ml/min). The desired fractions were collected and the solvent was evaporated, yielding 0.03 g of $N^4$-ethyl-$N^2$-methyl-$N^2$-[1-(phenylmethyl)-4-piperidinyl]-2,4-pyrimidinediamine (comp. 6)

EXAMPLE B.2

Using the same procedure as described in example B.1, but replacing 4-methyl-2-pentanone by N,N-dimethylformamide, intermediate 2 was reacted with 1-(2-chloroethyl)-3-methoxybenzene, to form $N^2$-[1-[2-(3-methoxyphenoxy)ethyl]-4-piperidinyl]-$N^2,N^4,N^4$-trimethyl-2,4-pyrimidinediamine (comp. 26, mp. 104.8° C.).

EXAMPLE B.3

Using the same procedure as describe in example B.1 and adding a small amount of potassium iodide to the reaction mixture. intermediate 2 was reacted with 1,1'-(4-chlorobutylidene)bis[4-fluorobenzene] to form $N^2$-[1-[4,4-bis(4-fluorophenyl)butyl]-4-piperidinyl]-$N^2,N^4,N^4$-trimethyl-2,4-pyrimidinediamine (comp. 44, mp. 106.3° C.).

EXAMPLE B.4

A mixture of chloromethylbenzene (1.9 g), intermediate 2 (3 g) and triethylamine (2.62 g) in N,N-dimethylacetamide (55 ml) was stirred for 2 hours at 75° C. The reaction mixture was poured out into ice-water and extracted with toluene. The separated organic layer was washed three times with water, dried, filtered and the solvent evaporated. The residue was dissolved in boiling petroleum ether and treated with activated charcoal. The mixture was filtered warm over dicalite, and the filtrate was concentrated. The concentrate was cooled on an ice-bath and the resulting precipitate was filtered off and dried, yielding 2.3 g (54.4%) of $N^2,N^4,N^4$-trimethyl-$N^2$-[1-(phenylmethyl)-4-piperidinyl]-2,4-pyrimidinediamine (comp. 8).

EXAMPLE B.5

A mixture of intermediate 4 (4.9 g) and 1,3-benzodioxole-5-carboxaldehyde (3 g) in methanol (250 ml) was hydrogenated at 50° C. with platinum on activated carbon (2 g) as a catalyst in the presence of thiophene (4%; 1 ml). After uptake of $H_2$, the catalyst was filtered off over dicalite, and the filtrate was evaporated. The residue was purified by column chromatography over silica gel (eluent: $CH_2Cl_2/CH_3OH$ 90/10). The pure fractions were collected and the solvent was evaporated. The residue was dissolved in methanol and converted into the ethanedioic acid salt (1:2). The precipitate was filtered off and dried, yielding 7.43 g (66.2%) of $N^2$-[1-(1,3-benzodioxol-5-ylmethyl)-4-piperidinyl]-$N^4$-cyclopropyl-$N^2$-methyl-2,4-pyrimidinediamine ethanedioate(1:2) (comp. 67).

EXAMPLE B.6

A mixture of 1-(2-phenylethyl)-4-piperidinamine (8.17 g) and 2-chloro-N,N-dimethyl-4-pyrimidinamine (6.3 g) was stirred for 20 hours at 120° C. The reaction mixture was diluted with water and extracted with $CH_2Cl_2$. The organic layer was washed with water, dried, filtered and the solvent evaporated. The residue was purified by column chromatography over silica gel (eluent: $CH_2Cl_2/CH_3OH(NH_3)$ 96/4). The pure fractions were collected and the solvent evaporated. The residue was crystallized from $CH_3CN$. The precipitate was filtered off and dried, yielding 3.69 g (28.4%) of $N^4,N^4$-dimethyl-$N^2$-[1-(2-phenylethyl)-4-piperidinyl]-2,4-pyrimidinediamine (comp. 11).

EXAMPLE B.7

A mixture of compound 67 (0.005 mol) and calciumcarbonate (0.0065 mol) in $CH_2Cl_2$ (25 ml) and methanol (10 ml) was stirred at room temperature. A solution of benzyltrimethylammonium dichloroiodate (0.005 mol) in $CH_2Cl_2$ (5 ml) and methanol (5 ml) was added dropwise at room temperature. The reaction mixture was stirred at room temperature for 30 minutes, then washed with water. The organic layer was separated, dried, filtered, and the solvent was evaporated. The residue was purified by column chromatography over silica gel (eluent: $CH_2Cl_2/CH_3OH$ 95/5). The pure fractions were collected and the solvent was evaporated. The residue (1.6 g) was dissolved in ethanol and converted into the (E)-2-butenedioic acid salt (3:2) with (E)-2-butenedioic acid. The precipitate was filtered off and dried, yielding 1.28 g (41.1%) of $N^2$-[1-(1,3-benzodioxol-5-ylmethyl)4-piperldinyl]-$N^4$-cyclopropyl-$N^2$-methyl-5-iodo-2,4-pyrimidinediamine. (E)-2-butenedioate (2:3) hydrate (1:1) (comp. 88).

EXAMPLE B.8

A mixture of compound 67 (1.6 mg), acetic acid (0.5 ml; 100%), $I^{125}$ (100 µCu) and $H_2O_2$ (0.1 ml) was stirred at room temperature. The reaction was quenced with sodiumsulfite solution (1.8 ml; 1M), yielding $N^2$-[1-(1,3-benzodioxol-5-ylmethyl)4-piperidinyl]-$N^4$-cyclopropyl-$N^2$-methyl-5-iodo-$^{125}$I-2,4-pyrimidinediamine (comp. 89). Tables 1 to 5 list compounds of formula (I) which were prepared according to one of the above examples.

TABLE 1

[Structure: Substituted phenyl-Alk-piperidine-N(R¹)-pyrimidine-N(R²)(R³) with Rˣ and Rʸ on phenyl ring]

| Co. No. | Ex No. | Rˣ | Rʸ | Alk | R¹ | R² | R³ | Phys. Data |
|---------|--------|-----|------|------|-----|-----|-----|------------|
| 1 | B.1 | H | H | $(CH_2)_4$ | $CH_3$ | $CH_3$ | $CH_3$ | — |
| 2 | B.1 | H | H | $(CH_2)_3$ | $CH_3$ | $CH_3$ | $CH_3$ | — |
| 3 | B.1 | H | H | $CH(CH_3)_2$ | $CH_3$ | $CH_3$ | $CH_3$ | — |
| 4 | B.1 | H | H | $CH_2$ | $(CH_2)_3CH_3$ | $CH_3$ | $CH_3$ | — |
| 5 | B.1 | H | H | $CH_2$ | $CH_3$ | cyclopropyl | H | — |
| 6 | B.1 | H | H | $CH_2$ | $CH_3$ | $CH_2CH_3$ | H | — |
| 7 | B.3 | H | H | $CH=CHCH_2$ | $CH_3$ | $CH_3$ | $CH_3$ | .(E)-2-butene-dioate/$H_2O$ |
| 8 | B.4 | H | H | $CH_2$ | $CH_3$ | $CH_3$ | $CH_3$ | — |
| 9 | B.5 | H | H | $CH_2$ | $CH_3$ | $CH_2CH_3$ | $CH_2CH_3$ | — |
| 10 | B.5 | H | H | $CH_2$ | $CH_3$ | $CH_3$ | H | — |
| 11 | B.6 | H | H | $(CH_2)_2$ | H | $CH_3$ | $CH_3$ | — |
| 12 | B.5 | H | 3-$CH_3$ | $CH_2$ | $CH_3$ | $CH_3$ | $CH_3$ | — |
| 13 | B.1 | H | 4-phenyl | $CH_2$ | $CH_3$ | $CH_3$ | $CH_3$ | — |
| 14 | B.1 | H | 2-Cl | $CH_2$ | $CH_3$ | $CH_3$ | $CH_3$ | — |
| 16 | B.1 | H | 2-F | $CH_2$ | $CH_3$ | $CH_3$ | $CH_3$ | — |
| 17 | B.1 | H | 3-F | $CH_2$ | $CH_3$ | $CH_3$ | $CH_3$ | — |
| 18 | B.1 | H | 3-$CF_3$ | $CH_2$ | $CH_3$ | $CH_3$ | $CH_3$ | — |
| 19 | B.1 | H | 4-$NO_2$ | $CH_2$ | $CH_3$ | $CH_3$ | $CH_3$ | — |
| 20 | B.1 | H | 4-Cl | $CH_2$ | $CH_3$ | $CH_3$ | $CH_3$ | — |
| 21 | B.1 | H | 3-$OCH_3$ | $CH_2$ | $CH_3$ | $CH_3$ | $CH_3$ | — |
| 22 | B.1 | H | 4-$OCH_3$ | $CH_2$ | $CH_3$ | $CH_3$ | $CH_3$ | — |
| 23 | B.1 | H | 3-Cl | $CH_2$ | $CH_3$ | $CH_3$ | $CH_3$ | — |
| 24 | B.1 | H | 4-F | $CH_2$ | $CH_3$ | $CH_3$ | $CH_3$ | — |
| 25 | B.2 | H | 2-$OCH_3$ | $CH_2$ | $CH_3$ | $CH_3$ | $CH_3$ | mp. 168.4° C./.2(COOH)$_2$ |
| 26 | B.2 | H | 3-$OCH_3$ | $CH_2$ | $CH_3$ | $CH_3$ | $CH_3$ | mp. 104.8° C. |
| 27 | B.4 | H | 4-Cl | $CH_2$ | $CH_3$ | $CH_3$ | $CH_3$ | — |
| 28 | B.5 | H | 2-$CH_3$ | $CH_2$ | $CH_3$ | $CH_3$ | $CH_3$ | — |
| 29 | B.5 | H | 4-$CH_3$ | $CH_2$ | $CH_3$ | $CH_3$ | $CH_3$ | — |
| 30 | B.5 | H | 2-$CF_3$ | $CH_2$ | $CH_3$ | $CH_3$ | $CH_3$ | — |
| 31 | B.5 | H | 4-$CF_3$ | $CH_2$ | $CH_3$ | $CH_3$ | $CH_3$ | — |
| 32 | B.5 | H | 2-$OCH_3$ | $CH_2$ | $CH_3$ | $CH_3$ | $CH_3$ | — |
| 33 | B.5 | H | 4-OH | $CH_2$ | $CH_3$ | $CH_3$ | $CH_3$ | — |
| 34 | B.5 | H | 4-$CH(CH_3)_2$ | $CH_2$ | $CH_3$ | $CH_3$ | $CH_3$ | |
| 35 | B.1 | 2-$CH_3$ | 5-$CH_3$ | $CH_2$ | $CH_3$ | $CH_3$ | $CH_3$ | |
| 36 | B.1 | 2-Cl | 6-Cl | $CH_2$ | $CH_3$ | $CH_3$ | $CH_3$ | |
| 37 | B.5 | 3-$OCH_3$ | 4-$OCH_3$ | $CH_2$ | $CH_3$ | $CH_3$ | $CH_3$ | |
| 38 | B.5 | H | H | $CH_2$ | $CH_3$ | —$(CH_2)_4$—* | | |

*: $R^2$ and $R^3$ are taken together to form a bivalent radical

TABLE 2

[Structure: bis(4-fluorophenyl)methyl-propyl-piperidine-N(R¹)-pyrimidine-N(R²)(R³)]

| Co. No. | Ex No. | R¹ | R² | R³ | Physical data |
|---------|--------|-----|-----|-----|---------------|
| 39 | B.3 | $CH_3$ | H | H | mp. 253.4° C./.2(COOH)$_2$ |
| 40 | B.3 | $CH_3$ | H | $CH_3$ | mp. 111.8° C. |
| 41 | B.3 | $CH_3$ | cyclopropyl | H | mp. 168.9° C./.2(COOH)$_2$ |
| 42 | B.3 | $CH_3$ | $CH_2CH_3$ | H | mp. 168.9° C./.2(COOH)$_2$ |
| 43 | B.3 | $CH_3$ | $(CH_2)_3CH_3$ | H | mp. 186.7° C./.2(COOH)$_2$ |

TABLE 2-continued

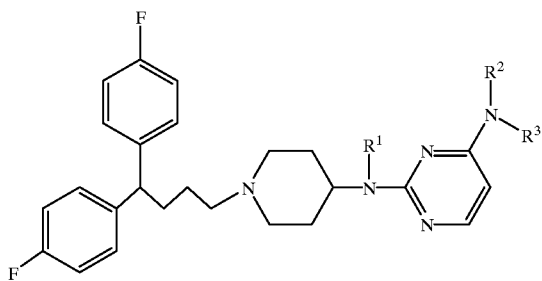

| Co. No. | Ex. No. | R¹ | R² | R³ | Physical data |
|---|---|---|---|---|---|
| 44 | B.3 | $CH_3$ | $CH_3$ | $CH_3$ | mp. 106.3° C. |
| 45 | B.3 | $CH_3$ | $CH(CH_3)_2$ | H | mp. 177.1° C./.3/2(COOH)$_2$ |
| 46 | B.3 | $(CH_2)_3CH_3$ | $CH_3$ | $CH_3$ | mp. 102.1° C. |
| 47 | B.3 | $CH_3$ | —$CH_2$—$CH_2$—$CH_2$—* | | mp. 173.2° C./.2(COOH)$_2$ |

*: R² and R³ are taken together to form a bivalent radical

TABLE 3

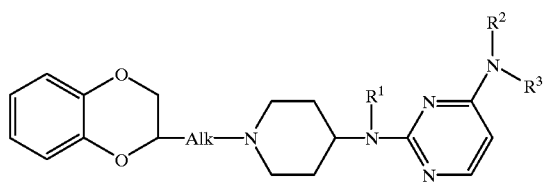

| Co. No. | Ex. No. | Alk | R¹ | R² | R³ | Physical data |
|---|---|---|---|---|---|---|
| 48 | B.1 | $CH_2$ | H | $CH_3$ | $CH_3$ | mp. 126.9° C. |
| 49 | B.4 | $CH_2$ | $CH_3$ | H | H | mp. 147.6° C. |
| 50 | B.1 | $CH_2$ | $CH_3$ | $CH_3$ | H | mp. 128.8° C. |
| 51 | B.4 | $CH_2$ | $CH_3$ | $CH_3$ | $CH_3$ | mp. 97.4° C. |
| 52 | B.1 | $CH_2$ | $CH_3$ | $(CH_2)_3CH_3$ | H | mp. 189.1° C./2(COOH)$_2$ |
| 53 | B.1 | $CH_2$ | $CH_3$ | $CH(CH_3)_2$ | H | mp. 194.2° C./2(COOH)$_2$ |
| 54 | B.1 | $CH_2$ | $CH_3$ | $CH_2CH_3$ | H | mp. 170° C./3/2(COOH)$_2$ |
| 55 | B.1 | $CH_2$ | $CH_3$ | cyclopropyl | H | mp. 166° C./.3/2(COOH)$_2$.H$_2$O |
| 56 | B.1 | $CH_2$ | $CH_3$ | $CH_2CH_3$ | $CH_2CH_3$ | mp. 153.9° C./.2(COOH)$_2$.H$_2$O |
| 57 | B.1 | $CH_2$ | $CH_2CH_3$ | $CH_3$ | $CH_3$ | mp. 141.7° C./.2(COOH)$_2$.H$_2$O |
| 58 | B.1 | $CH_2$ | $(CH_2)_3CH_3$ | $CH_3$ | $CH_3$ | mp. 132.5° C./2(COOH)$_2$ |
| 59 | B.1 | $CH_2$ | $(CH_2)_2CH_3$ | $(CH_2)_2CH_3$ | H | mp. 132.8° C./2(COOH)$_2$ |
| 60 | B.5 | $CH(CH_3)$ | $CH_3$ | $CH_3$ | $CH_3$ | mp. 211° C./.2(E)-2-butenedioate |
| 61 | B.1 | $CH_2$ | $CH_3$ | —$CH_2$—$CH_2$—$CH_2$—* | | mp. 107° C. |

*: R² and R³ are taken together to form a bivalent radical

TABLE 4

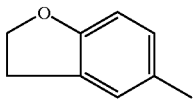

| Co. No. | Ex. No. | R¹ | R² | R³ | Physical data |
|---|---|---|---|---|---|
| 62 | B.5 | $CH_3$ | $CH_3$ | H | — |
| 63 | B.4 | $CH_3$ | $CH_3$ | $CH_3$ | mp. 127.1° C. |
| 64 | B.5 | $CH_3$ | $(CH_2)_2CH_3$ | $(CH_2)_2CH_3$ | — |
| 65 | B.5 | $CH_3$ | $CH_2CH_3$ | $CH_2CH_3$ | — |
| 66 | B.5 | $CH_3$ | cyclopropyl | H | — |
| 67 | B.5 | $CH_3$ | cyclopropyl | H | ethandioate (1:2) |
| 68 | B.5 | $CH_3$ | $CH_2CH_3$ | H | — |
| 69 | B.5 | $(CH_2)_3CH_3$ | $CH_3$ | $CH_3$ | — |
| 70 | B.5 | $CH_3$ | —$CH_2$—$CH_2$—$CH_2$—$CH_2$—* | | — |

*: R² and R³ are taken together to form a bivalent radical

TABLE 5

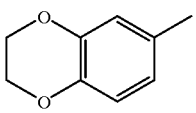

| Co. No. | Ex. No. | Q | Alk | Physical data |
|---|---|---|---|---|
| 71 | B.3 | phenoxy | —$CH(CH_3)CH_2$— | .2$(COOH)_2.H_2O$; mp. 142.5° C. |
| 72 | B.4 | phenoxy | $(CH_2)_2$ | .2$(COOH)_2$; mp. 192.6° C. |
| 73 | B.4 | phenoxy | $(CH_2)_4$ | .2$(COOH)_2$; mp. 162.8° C. |
| 74 | B.4 | 4-fluorophenoxy | $(CH_2)_3$ | mp. 113.8° C. |
| 75 | B.4 | 2-acetylphenoxy | $(CH_2)_2$ | mp. 133.2° C. |
| 76 | B.4 | 2-chloro-6-methylphenoxy | $(CH_2)_2$ | .2$(COOH)_2$; mp. 171.9° C. |
| 77 | B.1 | 2-pyridinyl | $CH_2$ | — |
| 78 | B.5 | 3-pyridinyl | $CH_2$ | — |
| 79 | B.5 | 4-pyridinyl | $CH_2$ | — |
| 80 | B.5 | 2-thienyl | $CH_2$ | — |
| 81 | B.1 | 1-naphthalenyl | $CH_2$ | — |
| 83 | B.5 | 2-naphthalenyl | $CH_2$ | — |
| 84 | B.1 | 2-quinolinyl | $CH_2$ | — |
| 85 | B.4 | 3-indolyl | $(CH_2)_2$ | mp. 201.2° C. |
| 86 | B.4 | 2,3-dihydrobenzofuran-5-yl | $CH_2$ | mp. 142.1° C. |
| 87 | B.2 | 2,3-dihydro-1,4-benzodioxin-6-yl | $CH_2$ | .3/2(E)-2-butenedioate; mp. 226.3° C. |

C. Pharmacological example

EXAMPLE C.1
In vitro binding affinity for dopamine $D_4$ receptor

The interaction of the compounds of formula (I) with the dopamine $D_4$ receptors was assessed in in vitro radioligand binding experiments.

A low concentration of $^3H$-spiperone with a high binding affinity for the dopamine $D_4$ receptor was incubated with a sample of a membrane preparation of transfected Chinese Hamster Ovary (CHO) cells which express cloned human $D_4$ receptors (Receptor Biology, Maryland, USA) in a buffered medium. When equilibrium of binding was reached, the receptor bound radioactivity was separated from the non-bound radioactivity, and the receptor bound activity was counted. The interaction of the test compounds, added to the incubation mixture in various concentrations, with the dopamine $D_4$ receptor was assessed in competition binding experiments as described by Schotte et al. (Psychopharmacology, 1996). The compounds with number 1, 2, 5–10, 12–14, 16–24, 26–32, 34–45, 52, 53, 55, 59, 61–63, 66, 68, 70, 73–76, 78, 80, 81 and 83–88 had a $pIC_{50}$ greater than or equal to 7 ($pIC_{50}$ is defined as $-\log IC_{50}$ wherein $IC_{50}$ is the concentration of the test compound causing an inhibition of 50% of the dopamine $D_4$ receptors).

D. Composition examples

"Active ingredient" (A.I.) as used throughout these examples relates to a compound of formula (I), a pharmaceutically acceptable addition salt or a stereochemically isomeric form thereof.

EXAMPLE D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.2

Film-coated tablets

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10,000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

EXAMPLE D.3

Oral solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound selected from the group consisting of:

$N^4$-cyclopropyl-$N^2$-methyl-$N^2$-[1-(phenylmethyl)-4-piperidinyl]-2,4-pyrimidinediamine;

$N^2$-[1-(1,3-benzodioxol-5-ylmethyl)-4-piperidinyl]-$N^4$-ethyl-$N^2$-methyl-2,4-pyrimidinediamine;

$N^2$-[1-(1,3-benzodioxol-5-ylmethyl)-4-piperidinyl]-$N^4$-cyclopropyl-$N^2$-methyl-2,4-pyrimidinediamine;

$N^2$-[1-[(4-chlorophenyl)methyl]-4-piperidinyl]-$N^2$,$N^4$,$N^4$-trimethyl-2,4-pyrimidinediamine;

$N^2$-[1-[(3-fluorophenyl)methyl]-4-piperidinyl]-$N^2$,$N^4$,$N^4$-trimethyl-2,4-pyrimidinediamine;

$N^2$,$N^4$,$N^4$-trimethyl-$N^2$-[1-[[4-(trifluoromethyl)phenyl]methyl]-4-piperidinyl]-2,4-pyrimidinediamine;

$N^2$,$N^4$,$N^4$-trimethyl-$N^2$-[1-[(4-methylphenyl)methyl]-4-piperidinyl]-2,4-pyrimidinediamine; and $N^2$,$N^4$,$N^4$-trimethyl-$N^2$-[1-[(3-methylphenyl)methyl]-4-piperidinyl]-2,4-pyrimidinediamine; a stereochemically isomeric form or a pharmaceutically acceptable addition salt thereof.

2. A method of treating a warm-blooded animal suffering from a psychotic disorder comprising administering to the warm-blooded animal a dopamine $D_4$ receptor antagonizing amount of a compound of formula (I)

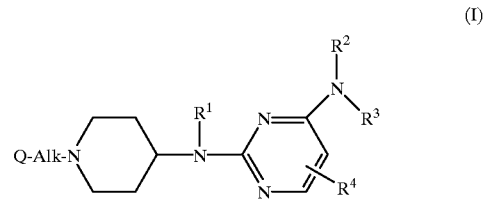

(I)

a N-oxide form, a pharmaceutically acceptable acid addition salt or a stereochemically isomeric form thereof, wherein Alk is $C_{1-6}$alkanediyl or $C_{3-6}$alkenediyl;

$R^1$ is hydrogen or $C_{1-4}$alkyl;

$R^2$ and $R^3$ each independently are hydrogen, $C_{1-6}$alkyl or $C_{3-7}$cycloalkyl; or $R^2$ and $R^3$ may also be taken together with the nitrogen atom to which they are attached, thus forming a pyrrolidine, a piperidine or a perhydro azepine ring;

$R^4$ is hydrogen or halo;

Q is aryl, aryloxy, di(aryl)methyl or heteroaryl;

aryl is naphthyl or phenyl, said naphthyl and phenyl may optionally be substituted with one, two or three substituents selected from halo, hydroxy, $C_{1-4}$alkyl, $C_{1-4}$alkyloxy, $C_{1-4}$alkylcarbonyl, halo$C_{1-4}$alkyl, nitro, amino, cyano and phenyl; and heteroaryl is quinolinyl, isoquinolinyl, pyridinyl, thienyl, indolyl, 2,3-dihydro-1,4-benzodioxinyl, 2,3-dihydrobenzofuranyl or benzodioxolanyl; said heteroaryls may optionally be substituted with one, two or three substituents selected from halo, hydroxy, $C_{1-4}$alkyl, $C_{1-4}$alkyloxy, $C_{1-4}$alkylcarbonyl, halo$C_{1-4}$alkyl and phenyl.

3. The method of claim 2, wherein the psychotic disorder is schizophrenia.

* * * * *